US011629335B2

(12) United States Patent
Liang et al.

(10) Patent No.: US 11,629,335 B2
(45) Date of Patent: Apr. 18, 2023

(54) METHODS OF IMPROVING VECTOR TRANSDUCTION EFFICIENCY INTO T LYMPHOCYTES

(71) Applicant: CELGENE CORPORATION, Summit, NJ (US)

(72) Inventors: Bitao Liang, Closter, NJ (US); Wei Liu, Bridgewater, NJ (US)

(73) Assignee: CELGENE CORPORATION, Summit, NJ (US)

( * ) Notice: Subject to any disclaimer, the term of this patent is extended or adjusted under 35 U.S.C. 154(b) by 98 days.

(21) Appl. No.: 17/200,745

(22) Filed: Mar. 12, 2021

(65) Prior Publication Data

US 2021/0309966 A1    Oct. 7, 2021

Related U.S. Application Data

(62) Division of application No. 15/325,376, filed as application No. PCT/US2015/039892 on Jul. 10, 2015, now Pat. No. 10,982,189.

(60) Provisional application No. 62/023,618, filed on Jul. 11, 2014.

(51) Int. Cl.
  *C12N 7/00* (2006.01)
  *A61K 39/00* (2006.01)
  *C12N 5/0783* (2010.01)
  *C12N 15/86* (2006.01)
  *C12N 15/87* (2006.01)

(52) U.S. Cl.
  CPC ............ *C12N 5/0636* (2013.01); *C12N 7/00* (2013.01); *C12N 15/86* (2013.01); *C12N 15/87* (2013.01); *C12N 2501/2302* (2013.01); *C12N 2501/51* (2013.01); *C12N 2501/515* (2013.01); *C12N 2501/727* (2013.01); *C12N 2510/02* (2013.01); *C12N 2740/15041* (2013.01); *C12N 2740/15042* (2013.01)

(58) Field of Classification Search
  None
  See application file for complete search history.

(56) References Cited

U.S. PATENT DOCUMENTS

| | | | |
|---|---|---|---|
| 5,665,577 A | 9/1997 | Sodroski et al. | |
| 5,948,893 A | 9/1999 | June et al. | |
| 5,994,136 A | 11/1999 | Naldini et al. | |
| 6,165,782 A | 12/2000 | Naldini et al. | |
| 6,352,694 B1 | 3/2002 | June et al. | |
| 6,428,953 B1 | 8/2002 | Naldini et al. | |
| 6,534,055 B1 | 3/2003 | June et al. | |
| 6,692,964 B1 | 2/2004 | June et al. | |
| 6,887,466 B2 | 5/2005 | June et al. | |
| 6,905,681 B1 | 6/2005 | June et al. | |
| 7,083,981 B2 | 8/2006 | Naldini et al. | |
| 7,250,299 B1 | 7/2007 | Naldini et al. | |
| 7,468,276 B2 | 12/2008 | Hariri et al. | |
| 7,741,465 B1 | 6/2010 | Eshhar et al. | |
| 8,057,788 B2 | 11/2011 | Hariri et al. | |
| 8,202,703 B2 | 6/2012 | Edinger et al. | |
| 8,263,065 B2 | 9/2012 | Hariri et al. | |
| 8,367,409 B2 | 2/2013 | Abbot et al. | |
| 9,765,342 B2 * | 9/2017 | Kochenderfer | ......... A61P 43/00 |
| 10,982,189 B2 | 4/2021 | Liang et al. | |
| 2005/0123514 A1 | 6/2005 | Davis et al. | |
| 2012/0093842 A1 | 4/2012 | Eshhar et al. | |
| 2012/0148553 A1 | 6/2012 | Hariri et al. | |
| 2017/0166866 A1 | 6/2017 | Liang et al. | |

FOREIGN PATENT DOCUMENTS

| | | |
|---|---|---|
| WO | WO 2007071440 | 6/2007 |
| WO | WO 2008153742 A2 | 12/2008 |
| WO | WO 2012072269 | 6/2012 |
| WO | WO 2013127964 | 9/2013 |
| WO | WO 2013154760 A1 | 10/2013 |
| WO | WO 2014/046617 | 3/2014 |
| WO | WO 2016007827 A1 | 1/2016 |

OTHER PUBLICATIONS

Sutlu et al. (Human Gene Therapy, 2012, p. 1090-1100).*
Addgene, LeGO-G2 (Plasmid #25917), Depositing Lab: Boris Fehse, [online] [retrieved on Feb. 7, 2020]. Retrieved from the Addgene Online Catalog using Internet:< URL: https://www.addgene.org/25917/> (4 pages).
Addgene, pCMV-VSV-G (Plasmid #8454), Depositing Lab: Bob Weinberg, [online] [retrieved on Feb. 7, 2020]. Retrieved from the Addgene Online Catalog using Internet:< URL: https://www.addgene.org/8454/> (4 pages).
Addgene, pMDLg/pRRE (Plasmid #12251), Depositing Lab: Didier Trono, [online] [retrieved on Feb. 7, 2020]. Retrieved from the Addgene Online Catalog using Internet:< URL: https://www.addgene.org/12251/> (4 pages).
Addgene, pRSV-Rev (Plasmid #12253), Depositing Lab: Didier Trono, [online] [retrieved on Feb. 7, 2020]. Retrieved from the Addgene Online Catalog using Internet:< URL: https://www.addgene.org/12253/> (4 pages).
Circosta et al., 2009, "T cell receptor (TCR) gene transfer with lentiviral vectors allows efficient redirection of tumor specificity in naive and memory T cells without prior stimulation of endogenous TCR," Hum. Gene Ther., 20(12): 1576-1588.
Extended European Search Report and EP Search Opinion dated Nov. 13, 2017 for EP Application No. 15818898.7.
Hyrup et al., 1996, "Peptide nucleic acids (PNA): synthesis, properties and potential applications," Bioorg. & Med. Chem., 4(1):5-23.
Kalvakolanu et al., 1991, "Enhancement of expression of exogenous genes by 2-aminopurine. Regulation at the post-transcriptional level," J. Biol. Chem., 266(2):873-879.

(Continued)

*Primary Examiner* — Agnieszka Boesen
(74) *Attorney, Agent, or Firm* — Morrison & Foerster LLP

(57) ABSTRACT

Provided herein are methods for enhancing the transduction efficiency of vectors into cells, e.g., primary human T lymphocytes.

22 Claims, 9 Drawing Sheets

(56) References Cited

OTHER PUBLICATIONS

Luhder et al., 2003, "Topological requirements and signaling properties of T cell-activating, anti-CD28 antibody superagonists," J Exp Med., 197(8):955-966.
Rajah and Chow, 2014, "The inhibition of human T cell proliferation by the caspase inhibitor z-VAD-FMK is mediated through oxidative stress," Toxicol, and Appl. Pharmacol., 278(2): 100-106.
Summerton et al., 1997, "Morpholino antisense oligomers: design, preparation, and properties," Antisense Nucleic Acid Drug Dev., 7(3): 187-195.
Sutlu et al., 2012, "Inhibition of intracellular antiviral defense mechanisms augments lentiviral transduction of human natural killer cells: implications for gene therapy," Hum. Gene Ther., 23(10):1090-1100.
Written Opinion and International Search Report dated Oct. 2, 2015 for PCT Application No. PCT/US2015/039892 filed Jul. 10, 2015 (WO 2016/007827).
Yang et al., 2010, "A Simplified Method for the Clinical-scale Generation of Central Memory-like CD8+ T Cells After Transduction With Lentiviral Vectors Encoding Antitumor Antigen T-cell Receptors," J. Immunotherapy, 33(6):648-658.

* cited by examiner

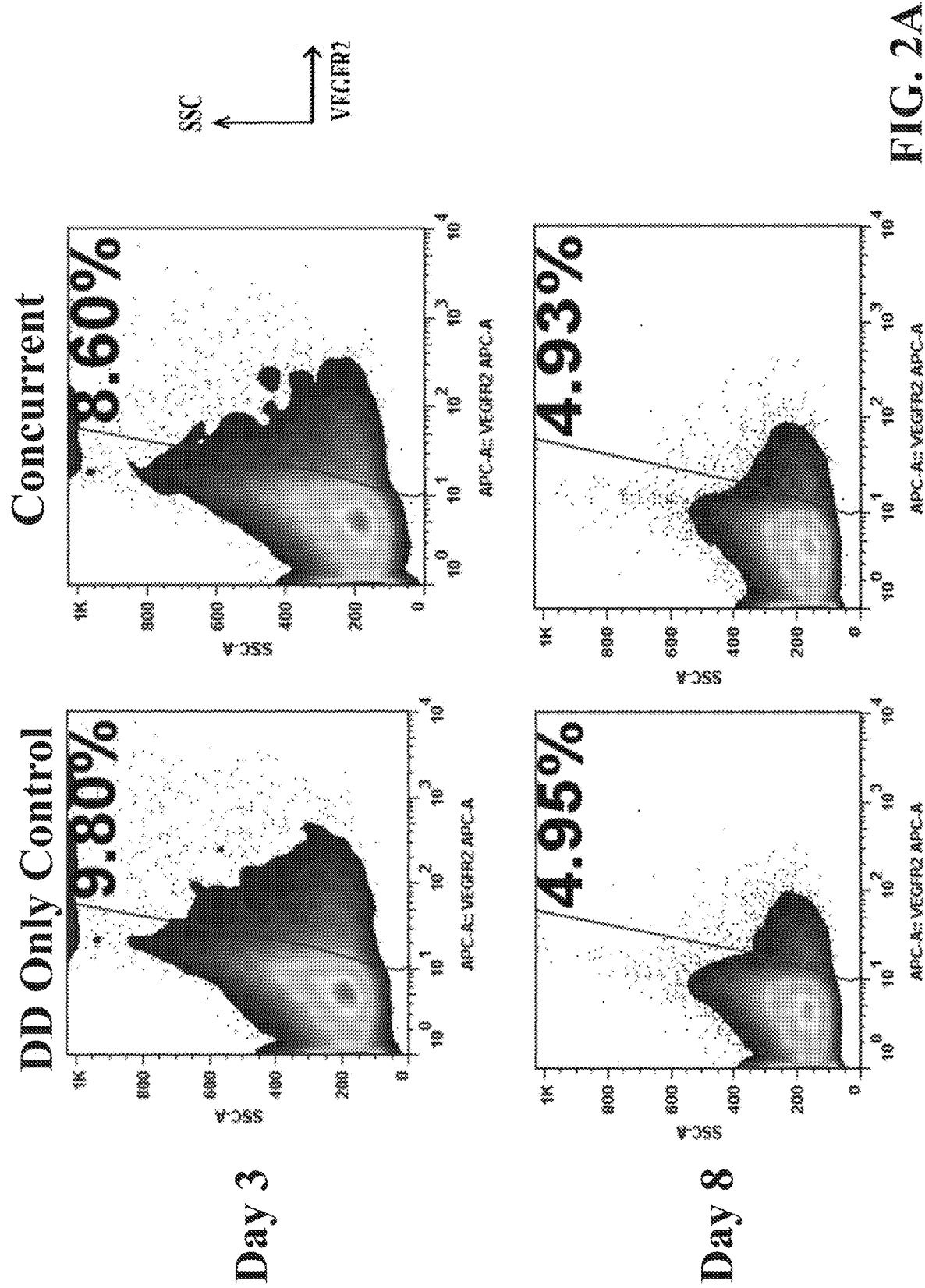

No Polycation

Mock (DD)

Mock (PS)

Isotype (BX795 2µM)

METHODS OF IMPROVING VECTOR TRANSDUCTION EFFICIENCY INTO T LYMPHOCYTES

This application is a divisional of U.S. application Ser. No. 15/325,376, filed Jan. 10, 2017, which is a National Stage entry of International Patent Application No. PCT/US2015/039892, filed Jul. 10, 2015, which claims the benefit of U.S. Provisional Patent Application No. 62/023,618, filed Jul. 11, 2014, each of which is incorporated by reference herein in its entirety.

1. FIELD

The disclosure herein relates to methods of improving transduction efficiency of vectors into cells.

2. BACKGROUND

T lymphocytes recognize and interact with specific antigens, including tumor-associated or tumor-specific antigens. Because T lymphocytes are able to kill tumor cells, the last 25 years have seen a great deal of interest in targeting tumor cells with T lymphocytes, either antigen-specific T lymphocytes, or T lymphocytes genetically modified to express one or more chimeric antigen receptors (CARs; see, e.g., Eshhar, U.S. Pat. No. 7,741,465; Eshhar, U.S. Patent Application Publication No. 2012/0093842). There is a need in the field for new methods to enhance the efficiency of CAR derivation from T lymphocytes.

3. SUMMARY

Provided herein are methods of enhancing the efficiency of producing genetically modified cells, for example immune cells, such as T lymphocytes, e.g., human T lymphocytes, for example primary T lymphocytes (e.g., primary human T lymphocytes). Without wishing to be bound by any particular mechanism or theory, it is thought that the innate immune system may inhibit the viral transduction step of CAR T cell production, and thus by inhibiting the activity of the innate immune system (e.g., inhibiting the ability of the innate immune system to inhibit viral transduction and/or subsequent viral protein production), CAR T cell derivation using vectors (e.g., viral vectors, e.g., retroviral vectors, for example lentiviral vectors) can be improved.

The methods provided herein may be used in conjunction with any type of cell, in particular, any mammalian cells, for example, any human cells, e.g., cells used for cell therapeutics, e.g., human cell therapeutics. Non-limiting examples of cells in which the methods may be used include, but are not limited to, natural killer (NK) cells (e.g., the placental intermediate natural killer cells disclosed in U.S. Pat. No. 8,263,065 or in U.S. Application No. 2012/0148553, the disclosures of which are hereby incorporated by reference in their entireties), dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), amnion-derived adherent cells (AMDACs) (e.g., the AMDACs disclosed in U.S. Pat. No. 8,367,409, the disclosure of which is hereby incorporated by reference in its entirety), tumor infiltrating lymphocytes, virus packaging cells (e.g., HEK 293T cells); mesenchymal-like stem cells (or mesenchymal stem cells or mesenchymal stromal cells) from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The methods may also be used in tumor cell lines, e.g., for animal model experimental purposes.

In certain embodiments, the methods described herein may include transducing (e.g., transducing with a retrovirus, for example a lentivirus) cells (e.g., primary human T lymphocytes). In certain embodiments, the methods described herein may include contacting cells, (e.g., primary human T lymphocytes) with a compound that is an inhibitor of the innate immune system either before, concurrently with, or after said transduction (e.g., retroviral transduction, for example lentiviral transduction). In a particular embodiment, transduction (e.g., retroviral transduction, for example lentiviral transduction) introduces into the cells an isolated nucleic acid greater than 10 kilobases. In yet another embodiment, the isolated nucleic acid transduced into the cells (e.g., via retroviral transduction, for example lentiviral transduction into primary human T lymphocytes), for example, a vector, e.g., a viral vector, encodes one or more proteins, for example, encodes one or more chimeric antigen receptors.

In a particular embodiment, the compound used in the methods described herein to contact said cells (e.g., primary human T lymphocytes) during transduction (e.g., retroviral transduction, for example lentiviral transduction) is an inhibitor of the innate immune system. In a particular embodiment, said inhibitor of the innate immune system is an inhibitor of IκB kinase ε (IKK ε) and/or TANK-binding kinase 1 (TBK1). In a specific embodiment, said compound is BX795. In a specific embodiment, said inhibitor of the innate immune system is an inhibitor of protein kinase R (PKR). In a specific embodiment, said compound is 2-Aminopurine (2-AP).

In one embodiment of the methods described herein, cells (e.g., primary human T lymphocytes) are contacted with a compound described herein (e.g., BX795 or 2-AP) before, concurrently with, or after transduction with a vector, for example, a viral vector (e.g., retroviral transduction, for example lentiviral transduction). In another embodiment, cells (e.g., primary human T lymphocytes) are contacted with a compound described herein (e.g., BX795 or 2-AP) 30 minutes, 60 minutes, 2 hours or 3 hours prior to transduction with a viral vector (e.g., retroviral transduction, for example lentiviral transduction). In another embodiment, cells (e.g., primary human T lymphocytes) are contacted with a compound described herein (e.g., BX795 or 2-AP) concurrently with transduction with a viral vector (e.g., retroviral transduction, for example lentiviral transduction) and for a period of 2 hours, 4 hours, or 6 hours thereafter. In another embodiment, cells (e.g., primary human T lymphocytes) are contacted with a compound described herein (e.g., BX795 2-AP) for 30 minutes, 60 minutes, 2 hour or 3 hours before transduction with a viral vector (e.g., retroviral transduction, for example lentiviral transduction) and concurrently with transduction (e.g., retroviral transduction, for example lentiviral transduction) for a period of 2 hours, 4 hours, or 6 hours thereafter. In a specific embodiment, said compound described herein (e.g., BX795 or 2-AP) is used at a concentration of 1-20 PM. In another embodiment, said compound described herein (e.g., BX795 or 2-AP) is used at a concentration of 2.5-10 μM. In yet another embodiment, said compound described herein (e.g., BX795 or 2-AP) is used at a concentration of 4-8 μM.

In one embodiment, the methods provided herein additionally comprise contacting cells (e.g., primary human T lymphocytes) with a transformation reagent (e.g., diethylaminoethyl-dextran or protamine sulfate) prior to or concurrently with transduction with a vector, for example, a viral vector (e.g., retroviral transduction, for example lentiviral transduction).

In one embodiment of the methods described herein, cells (e.g., primary human T lymphocytes) are additionally contacted with an agent capable of stimulating a T cell receptor complex before transduction with a vector, for example, a viral vector (e.g., retroviral transduction, for example lentiviral transduction). In a particular embodiment, said agent is an antibody or antigen binding fragment. In a particular embodiment, said antibody or antigen binding fragment(s) specifically binds CD3 and/or CD28. In a particular embodiment, said antibody or antigen binding fragment is coupled to a solid substrate (e.g., Dynabeads®). In another particular embodiment, said antibody or antigen binding fragment(s) (e.g., anti-CD3 and/or anti-CD28) are not present on a solid surface, e.g., the same solid surface, but are instead present in solution, or complexed with another compound or composition that allows presentation of the antibody or antigen binding fragment(s) to the cell, e.g., the antibody or antigen binding fragment(s) are complexed with a polymer, hydrogel, albumin, and/or a hydrophobic molecule. In certain embodiments, the molecule to which the antibody or antigen binding fragment(s) are complexed is not an adjuvant. In another embodiment, said contacting occurs at least 48 hours, at least 44 hours, at least 40 hours, at least 36 hours, at least 32 hours, at least 28 hours, at least 24 hours, at least 20 hours, at least 16 hours, at least 12 hours, at least 8 hours or at least 4 hours prior to transduction of said cells with a vector, for example a viral vector (e.g., retroviral transduction, for example lentiviral transduction).

In a particular embodiment of the methods described herein, cells (e.g., primary human T lymphocytes) are transduced with a virus (e.g., a retrovirus, for example a lentivirus) at a multiplicity of infection (MOI) of 1.5 to 3.0.

In a specific embodiment, provided herein is a method of transducing primary T lymphocytes (e.g., human primary T lymphocytes), comprising: contacting primary T lymphocytes with i) a viral vector (e.g., retoviral vector, for example a lentiviral vector) comprising a nucleic acid and ii) a compound that is an inhibitor of the innate immune system, such that the nucleic acid is transduced into the T lymphocytes. In another specific embodiment, said contacting of said primary T lymphocytes with said compound occurs before (e.g., 30 minutes before, 1 hour before, 2 hours before, 3 hours before, 4 hours before, 6 hours before, 7 hours before, 8 hours before, 9 hours before or 10 hours before) and/or concurrently with contacting of said T lymphocytes with said viral vector. In another specific embodiment, said viral vector comprises a nucleic acid encoding one or more protein, for example, one or more chimeric antigen receptors (CARs).

In another specific embodiment, said compound inhibits the activity of IκB kinase ε (IKK c) or TANK-binding kinase 1 (TBK1). In another specific embodiment, said compound that inhibits the activity of IκB kinase ε (IKK c) or TANK-binding kinase 1 (TBK1) is BX795 (e.g., 1 μM, 2 μM, 3 μM, 4 μM, 5 μM, 6 μM, 7 μM, 8 μM, 9 μM or 10 μM BX795). In another specific embodiment, said compound inhibits the activity of protein kinase R (PKR). In another specific embodiment, said compound that inhibits the activity of protein kinase R (PKR) is 2-Aminopurine (2-AP) (e.g., 1 μM, 2 μM, 2.5 μM, 3 μM, 4 μM, 5 μM, 6 μM, 7 μM, 8 μM, 9 μM or 10 μM 2-AP).

In another specific embodiment, the method of transducing primary T lymphocytes further comprises contacting said primary T lymphocytes with an agent capable of stimulating a T cell receptor complex prior to contacting the primary T lymphocytes with the viral vector. In a specific embodiment, said agent is an antibody or antigen-binding fragment, e.g., an antibody or antigen-binding fragment that specifically binds to CD3 and/or CD28. In another specific embodiment, the method of transducing primary T lymphocytes further comprises contacting the primary T lymphocytes with a transformation reagent (e.g., diethylaminoethyl-dextran or protamine sulfate) and, optionally, a cytokine (e.g., interleukin 2 (IL-2), interleukin 7 (IL-7), interleukin 12 (IL-12), interleukin 15 (IL-15) or interleukin 21 (IL-21)).

In another specific embodiment, provided herein is a method of transducing primary T lymphocytes (e.g., human primary T lymphocytes), comprising: contacting human primary T lymphocytes, in the presence of diethylaminoethyl-dextran or protamine sulfate and interleukin 2, with i) a retroviral vector, for example a lentiviral vector comprising a nucleic acid encoding one or more proteins, for example, one or more chimeric antigen receptors, and ii) BX795 (e.g., 6 μM BX795), such that the nucleic acid is transduced into the T lymphocytes. In a specific embodiment, said contacting of said primary T lymphocytes with BX795 occurs before (e.g., 3 hours before, 6 hours before) and/or concurrently with contacting of said T lymphocytes with said viral vector. In another specific embodiment, said vector comprises a nucleic acid encoding one or more chimeric antigen receptors.

In another specific embodiment, provided herein is a method of transducing primary T lymphocytes (e.g., human primary T lymphocytes), comprising: contacting human primary T lymphocytes, in the presence of diethylaminoethyl-dextran or protamine sulfate and interleukin 2 (IL-2), with i) a retroviral vector, for example a lentiviral vector comprising a nucleic acid encoding a chimeric antigen receptor and ii) 6 μM BX795, wherein the contacting of the human primary T lymphocytes with the 6 μM BX795 occurs for about 3 hours, followed by at least 6 hours of concurrently contacting the human primary T lymphocytes with the viral vector and the 6 μM BX795, so that the nucleic acid is transduced into the T lymphocytes. In another specific embodiment, said vector comprises a nucleic acid encoding one or more chimeric antigen receptors.

In another specific embodiment, provided herein is a method of transducing primary T lymphocytes (e.g., human primary T lymphocytes), comprising: contacting human primary T lymphocytes, in the presence of diethylaminoethyl-dextran or protamine sulfate and interleukin 2, with i) a retroviral vector, for example a lentiviral vector comprising a nucleic acid encoding a chimeric antigen receptor and ii) 2-AP (e.g., 2.5-10 μM 2-AP), such that the nucleic acid is transduced into the T lymphocytes. In a specific embodiment, said contacting of said primary T lymphocytes with 2-AP occurs before (e.g., 90 minutes before, 2 hours before, or 3 hours before) and/or concurrently with contacting of said T lymphocytes with said viral vector. In another specific embodiment, said vector comprises a nucleic acid encoding one or more chimeric antigen receptors.

In another specific embodiment, provided herein is a method of transducing primary T lymphocytes (e.g., human primary T lymphocytes), comprising: contacting human primary T lymphocytes, in the presence of diethylaminoethyl-dextran or protamine sulfate and interleukin 2, with i) a retroviral vector, for example a lentiviral vector comprising a nucleic acid encoding a chimeric antigen receptor and ii) 2.5-10 μM 2-AP, wherein the contacting of the human primary T lymphocytes with the 2.5-10 μM 2-AP occurs for 90 minutes, followed by at least 5 hours of concurrently contacting the human primary T lymphocytes with the viral vector and the 2.5-10 μM 2-AP, so that the nucleic acid is transduced into the T lymphocytes. In another specific embodiment, said vector comprises a nucleic acid encoding one or more chimeric antigen receptors.

4. BRIEF DESCRIPTION OF THE FIGURES

FIGS. 1A-1C show the effects of concurrent treatment of DEAE-dextran alone (FIG. 1A) or with BX795 in the presence of DEAE-dextran (FIGS. 1B and 1C, at concentrations of 1 μM, 2 μM, 4 μM, 6 μM, 8 μM and 10 μM) on the transduction efficiency of primary T lymphocytes using chimeric antigen receptor-encoding lentiviruses.

FIGS. 2A and 2B shows the effects of BX795 treatment on the efficiency of lentiviral transduction. Transduction efficiency of primary T lymphocytes transduced with chimeric antigen receptor-encoding lentiviruses was assessed for various conditions: (i) BX795 pretreatment, (ii) BX795 concurrent treatment, (iii) a combination of BX795 pretreatment and concurrent treatment and (iv) a control treatment.

5. DETAILED DESCRIPTION

Figure 1A:
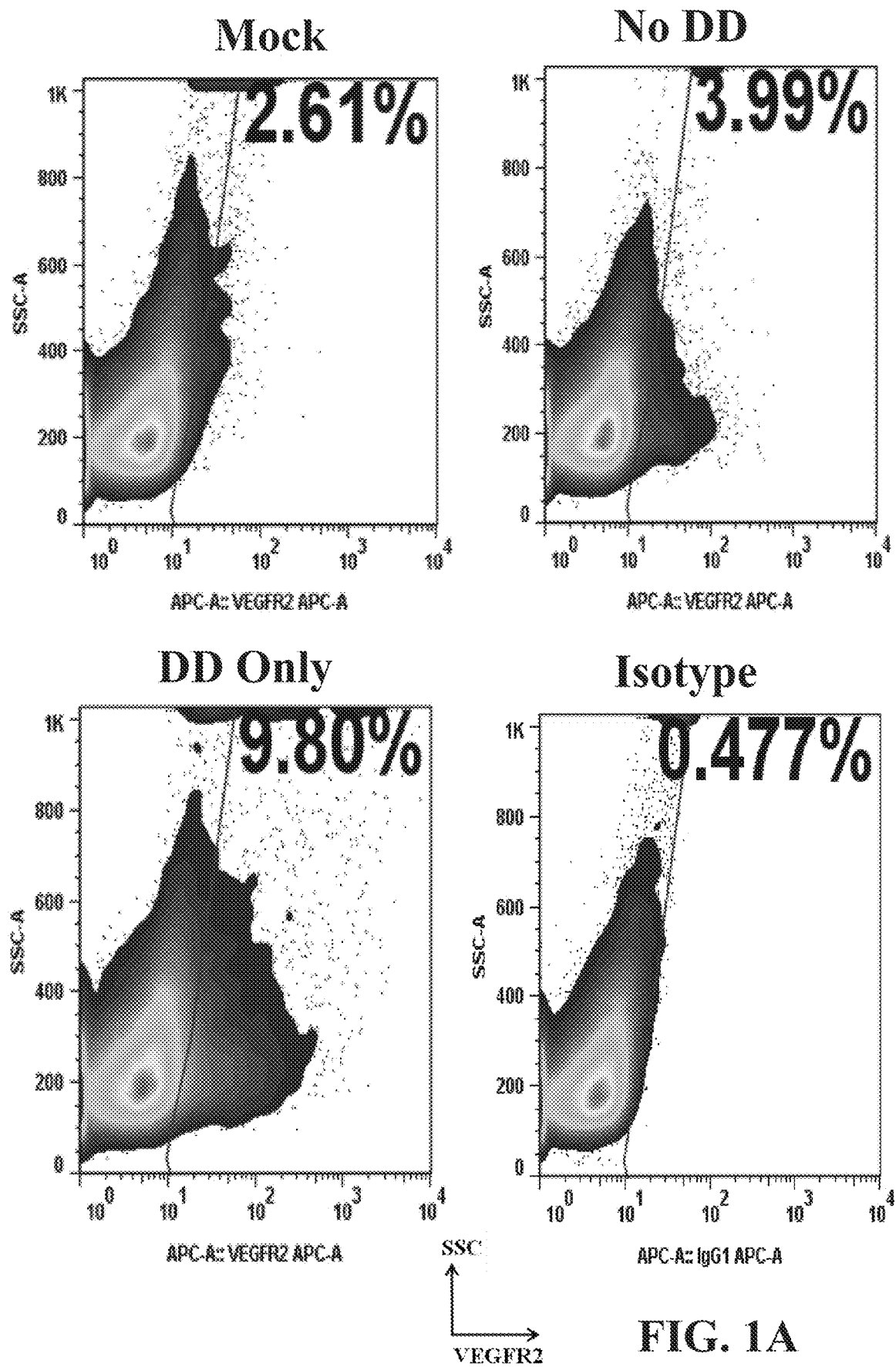

5.1. Methods of Transduction
5.1.1. Cells

Non-limiting examples of cells that can be used in the methods described herein include T lymphocytes, dendritic cells (DC), placental stem cells (e.g., the placental stem cells disclosed in U.S. Pat. Nos. 7,468,276; 8,057,788 and 8,202,703, the disclosures of which are hereby incorporated by reference in their entireties), mesenchymal-like stem cells from umbilical cord blood, placental blood, peripheral blood, bone marrow, dental pulp, adipose tissue, osteochondral tissue, and the like; embryonic stem cells, embryonic germ cells, neural crest stem cells, neural stem cells, and differentiated cells (e.g., fibroblasts, etc.). The methods may also be used in tumor cell lines, e.g., for animal model experimental purposes. In a particular embodiment, the cells of the methods described herein may be primary cells. Primary cells are well known in the art and may include cells extracted from a subject (e.g., a human) that are cultured or expanded in vitro for an amount of time that does not lead to the onset of cellular senescence, and are not cultured or expanded in a manner that leads to immortalization of the cells. In a specific embodiment, the cells used in the methods described herein are human T lymphocytes. In another specific embodiment, the cells used in the methods described herein are not natural killer cells. In another specific embodiment, the cells used in the methods described herein are not T lymphocyte cell lines.

In a specific embodiment, the cells used in the methods provided herein are primary T lymphocytes (e.g., primary human T lymphocytes). The primary T lymphocytes used in the methods provided herein may be naive T lymphocytes or MHC-restricted T lymphocytes. In certain embodiments, the T lymphocytes are CD4$^+$. In other embodiments, the T lymphocytes are CD8$^+$. In certain embodiments, the primary T lymphocytes are tumor infiltrating lymphocytes (TILs). In certain embodiments, the primary T lymphocytes have been isolated from a tumor biopsy, or have been expanded from T lymphocytes isolated from a tumor biopsy. In certain embodiments, the primary T lymphocytes have been isolated from, or are expanded from T lymphocytes isolated from, peripheral blood, cord blood, or lymph. In certain embodiments, the T lymphocytes are allogeneic with respect to a particular individual, e.g., a recipient of said T lymphocytes. In certain other embodiments, the T lymphocytes are not allogeneic with respect to a certain individual, e.g., a recipient of said T lymphocytes. In certain embodiments, the T lymphocytes are autologous with respect to a particular individual, e.g., a recipient of said T lymphocytes.

In one embodiment, primary T lymphocytes are obtained from an individual, optionally expanded, and then transduced, using the methods described herein, with a nucleic acid encoding one or more chimeric antigen receptors (CARs), and optionally then expanded. See Section 5.2. T lymphocytes can be expanded, for example, by contacting the T lymphocytes in culture with antibodies to CD3 and/or CD28, e.g., antibodies attached to beads, or to the surface of a cell culture plate; see, e.g., U.S. Pat. Nos. 5,948,893; 6,534,055; 6,352,694; 6,692,964; 6,887,466; and 6,905,681. In specific embodiments, the antibodies are anti-CD3 and/or anti-CD28, and the antibodies are not bound to a solid surface (e.g., the antibodies contact the T lymphocytes in solution). In other specific embodiments, either of the anti-CD3 antibody or anti-CD28 antibody is bound to a solid surface (e.g. bead, tissue culture dish plastic), and the other antibody is not bound to a solid surface (e.g., is present in solution).

In certain embodiments, primary T lymphocytes used in the methods described herein are isolated from a tumor, e.g., are tumor-infiltrating lymphocytes. In particular embodiments, such T lymphocytes are specific for a tumor specific antigen (TSA) or tumor associated antigen (TAA). See Section 5.2.2.

5.1.2. Transformation Reagents

As used herein, terms such as "transduction," "transformation," and "transfection" are used interchangeably, unless otherwise noted. Methods of transducing cells are well-known in the art. During transduction, small molecules and/or polymers may, for example, be added to cell cultures to facilitate the binding and/or uptake of the proteins and/or nucleic acids of interest. Particularly, small polar compounds can be added to culture conditions to facilitate the binding and transduction of viruses and nucleic acid(s) therein. Exemplary transformation reagents include, without limitation, Lipofectamine®, FuGENE®, calcium phosphate, diethylaminoethyl cellulose-dextran (DEAE-dextran or DD), and protamine sulfate. In certain embodiments of the methods described herein, transduction (e.g., retroviral transduction, for example lentiviral transduction) of T lymphocytes (e.g., primary human T lymphocytes) occurs in the presence of the DEAE-dextran or protamine sulfate. In particular embodiments of the methods described herein, transduction (e.g., retroviral transduction, for example lentiviral transduction) of T lymphocytes (e.g., primary human T lymphocytes) occurs in the presence of DEAE-dextran, e.g., 10 μg/ml DEAE-dextran, or protamine sulfate, e.g., 10 μg/ml protamine sulfate.

5.1.3. Culture Conditions and T Lymphocyte Activation

The cells described herein can be maintained under specific culturing conditions to facilitate or enhance transduction (e.g. viral transduction). In a particular embodiment, T lymphocytes (e.g., primary human T lymphocytes) are activated by an antigen or antigen-binding fragment that specifically binds to a T lymphocyte co-stimulatory molecule (e.g., CD28, CD3 and/or CD45) prior to or concurrently with transduction. In another embodiment, said antibody or antigen-binding fragment is coupled to a solid substrate (e.g., Dynabeads®). In a particular embodiment, T lymphocytes (e.g., primary human T lymphocytes) are stimulated by anti-CD3, anti-CD28, and/or anti-CD45 antibodies, or antigen binding fragment(s) thereof, coupled to Dynabeads® for 24 hours before transduction (e.g., viral transduction). In another particular embodiment, said antibody or antigen binding fragment(s) (e.g., of anti-CD3, anti-CD28 and/or anti-CD45 antibodies or antigen binding fragment(s) thereof) are not present on a solid substrate but are instead complexed with another compound or composition that allows presentation of the antibody or antigen binding fragment(s) to the cell, e.g., the antibody or antigen binding fragment(s) are complexed with a polymer, hydrogel, albumin, and/or a hydrophobic molecule. In particular embodiments, such molecule(s) complexed with the antibody or antigen binding fragment(s) thereof is not an adjuvant. In another embodiment, said contacting occurs at least 48 hours, at least 44 hours, at least 40 hours, at least 36 hours, at least 32 hours, at least 28 hours, at least 24 hours, at least 20 hours, at least 16 hours, at least 12 hours, at least 8 hours or at least 4 hours prior to transduction of said cells with a viral vector (e.g., retroviral transduction, for example lentiviral transduction). In yet another embodiment, said contacting occurs at least 48 hours to 40 hours, 44 hours to 36 hours, 40 hours to 32 hours, 36 hours to 28 hours, 32 hours to 24 hours, 28 hours to 20 hours, 24 hours to 16 hours, 20 hours to 12 hours, 16 hours to 8 hours, 12 hours to 4 hours or at least 8 hours to 1 hour prior to transduction of said cells with a viral vector (e.g., retroviral transduction, for example lentiviral transduction).

In another embodiment, cytokines and/or growth factors that stimulate T lymphocyte activation and/or proliferation can be added prior to or concurrently with transduction. In a particular embodiment, interleukin 2 (IL-2), e.g., 50 U/ml IL-2, is added to T lymphocyte cultures (e.g., primary human T lymphocyte cultures) prior to or concurrently with transduction (e.g., viral transduction). In another embodiment, interleukin 7 (IL-7), e.g., 10 ng/ml IL-7, is added to T lymphocyte cultures (e.g., primary human T lymphocyte cultures) prior to or concurrently with transduction (e.g., viral transduction). In another embodiment, interleukin 12 (IL-12), e.g., 10 ng/ml IL-12, is added to T lymphocyte cultures (e.g., primary human T lymphocyte cultures) prior to or concurrently with transduction (e.g., viral transduction). In another embodiment, interleukin 15 (IL-15), e.g., 10 ng/ml IL-15, is added to T lymphocyte cultures (e.g., primary human T lymphocyte cultures) prior to or concurrently with transduction (e.g., viral transduction). In yet another embodiment, interleukin 21 (IL-21), e.g., 25 ng/ml IL-21 is added to T lymphocyte cultures (e.g., primary human T lymphocyte cultures) prior to or concurrently with transduction (e.g., viral transduction).

5.1.4. Inhibitors of Innate Immunity

The innate immune system can repress expression of genes of viruses, including synthetic viruses. It is well known in the art that the innate immune system comprises proteins (e.g., retinoic acid-inducible gene I (RIG-I), protein kinase R (PKR), IκB kinase ε (IKK E), TANK-binding kinase 1 (TBK1)) that can be triggered by double stranded RNA and other pathogenic macromolecules, and that innate immune activity can be readily measured (e.g., secreted levels of interferon proteins including but not limited to interferon-α, interferon-β, interferon-δ, interferon-ζ, interferon-κ and interferon-τ). Accordingly, in a particular embodiment of the methods described herein, cultured cells are contacted with an inhibitor of innate immunity. In another embodiment, transduction (e.g., retroviral transduction, for example lentiviral transduction) of T lymphocytes (e.g., primary human T lymphocytes) can be enhanced by the addition of compounds, for example small molecules, that inhibit innate immune signaling (e.g., BX795, Piceatannol, Gefitinib, Z-VAD-FMK, Glybenclamide, Pepinh-MyD, OxPAPC, CLI-095, Polymyxin B, H-89, 2-Aminopurine (2-AP), Chloroquine, Bafilomycin A1 or the like).

In certain embodiments of the methods described herein, transduction (e.g., retroviral transduction, for example lentiviral transduction) of T lymphocytes (e.g., primary human T lymphocytes) can be enhanced by contacting the T lymphocytes with an inhibitor of the innate immune response either before, concurrently with or after transduction. In a specific embodiment of the methods described herein, transduction (e.g., retroviral transduction, for example lentiviral transduction) of T lymphocytes (e.g., primary human T lymphocytes) can be enhanced upon treatment with an inhibitor of IκB kinase ε (IKK E) and/or TANK-binding kinase 1 (TBK1) either before, concurrently with or after transduction. In another specific embodiment of the methods described herein, transduction (e.g., retroviral transduction, for example lentiviral transduction) of T lymphocytes (e.g., primary human T lymphocytes) can be enhanced upon treatment with BX795 either before, concurrently with or after transduction of the cells.

In a specific embodiment of the methods described herein, transduction (e.g., retroviral transduction, for example lentiviral transduction) of T lymphocytes (e.g., primary human T lymphocytes) can be enhanced upon treatment with BX795 at a concentration of 0.5 μM, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, or greater. In another specific embodiment of the methods described herein, transduction (e.g., retroviral transduction, for example lentiviral transduction) of T lymphocytes (e.g., primary human T lymphocytes) can be enhanced upon treatment with BX795 at a concentration of 0.5 μM to 1 μM, 1 μM to 3 μM, 2 μM to 4 μM, 3 μM to 5 μM, 4 μM to 6 μM, 5 μM to 7 μM, 6 μM to 8 μM, 7 μM to 9 μM, 8 μM to 10 μM, 9 μM to 11 μM, 10 μM to 12 μM, 11 μM to 13 μM, 12 μM to 14 μM or 13 μM to 15 μM, 10 μM to 20 μM, 10 μM to 15 μM or 10 μM to 12 μM.

In certain embodiments of the methods described herein, transduction (e.g., retroviral transduction, for example lentiviral transduction) of T lymphocytes (e.g., primary human T lymphocytes) can be enhanced upon treatment with BX795 before transduction of the cells. For example, in certain embodiments of the methods described herein, transduction (e.g., retroviral transduction, for example lentiviral transduction) of T lymphocytes (e.g., primary human T lymphocytes) can be enhanced upon treatment with BX795 for greater than 5 hours before transduction, 5 hours before transduction, 4 hours before transduction, 3 hours before transduction, 2 hours before transduction, 1 hour before transduction, 30 minutes before transduction, 15 minutes before transduction, 5 minutes before transduction or concurrently with transduction. In a specific embodiment of the methods described herein, transduction (e.g., retroviral transduction, for example lentiviral transduction) of T lymphocytes (e.g., primary human T lymphocytes) can be enhanced upon treatment with BX795 4 to 5 hours before transformation, 3 to 4 hours before transduction, 2 to 3 hours before transduction, 1 to 2 hours before transduction, 30 minutes to 1 hour before transduction or concurrently to 30 minutes before transduction. In a specific embodiment of the methods described herein, transduction (e.g., retroviral transduction, for example lentiviral transduction) of T lymphocytes (e.g., primary human T lymphocytes) can be enhanced upon treatment with BX795 both before and concurrently with transduction at any of the time points described herein.

In a specific embodiment, said inhibitor of the innate immune system is an inhibitor of protein kinase R (PKR). In a specific embodiment of the methods described herein, transduction (e.g., retroviral transduction, for example lentiviral transduction) of T lymphocytes (e.g., primary human T lymphocytes) can be enhanced upon treatment with an inhibitor of protein kinase R (PKR) either before, concurrently with or after transduction. In a specific embodiment, said compound is 2-Aminopurine (2-AP).

In certain embodiments of the methods described herein, transduction (e.g., retroviral transduction, for example lentiviral transduction) of T lymphocytes (e.g., primary human T lymphocytes) can be enhanced upon treatment of the T lymphocytes with an inhibitor of the innate immune response either before, concurrently with or after transduction. In a specific embodiment of the methods described herein, transduction (e.g., retroviral transduction, for example lentiviral transduction) of T lymphocytes (e.g., primary human T lymphocytes) can be enhanced upon treatment with an inhibitor of protein kinase R (PKR) either before, concurrently with or after transduction. In another specific embodiment of the methods described herein, transduction (e.g., retroviral transduction, for example lentiviral transduction) of T lymphocytes (e.g., primary human T lymphocytes) can be enhanced upon treatment with 2-AP either before, concurrently with or after transduction of the cells.

In a specific embodiment of the methods described herein, transduction (e.g., retroviral transduction, for example lentiviral transduction) of T lymphocytes (e.g., primary human T lymphocytes) can be enhanced upon treatment with 2-AP at a concentration of 0.5 µM, 1 µM, 2 µM, 3 µM, 4 µM, 5 µM, 6 µM, 7 µM, 8 µM, 9 µM, 10 µM, 11 µM, 12 µM, 13 µM, 14 µM, 15µM or greater. In another specific embodiment of the methods described herein, transduction (e.g., retroviral transduction, for example lentiviral transduction) of T lymphocytes (e.g., primary human T lymphocytes) can be enhanced upon treatment with 2-AP at a concentration of 0.5 µM to 1 µM, 1 µM to 3 µM, 2 µM to 4 µM, 3 µM to 5 µM, 4 µM to 6 µM, 5 µM to 7 µM, 6 µM to 8 µM, 7 µM to 9 µM, 8 µM to 10 µM, 9 µM to 11 µM, 10 µM to 12 µM, 11 µM to 13 µM, 12 µM to 14 µM or 13 µM to 15 µM.

In certain embodiments of the methods described herein, transduction (e.g., retroviral transduction, for example lentiviral transduction) of T lymphocytes (e.g., primary human T lymphocytes) can be enhanced upon treatment with 2-AP before transduction of the cells. For example, in certain embodiments of the methods described herein, transduction (e.g., retroviral transduction, for example lentiviral transduction) of T lymphocytes (e.g., primary human T lymphocytes) can be enhanced upon treatment with 2-AP for greater than 5 hours before transduction, 5 hours before transduction, 4 hours before transduction, 3 hours before transduction, 2 hours before transduction, 1 hour before transduction, 30 minutes before transduction, 15 minutes before transduction, 5 minutes before transduction or concurrently with transduction. In a specific embodiment of the methods described herein, transduction (e.g., retroviral transduction, for example lentiviral transduction) of T lymphocytes (e.g., primary human T lymphocytes) can be enhanced upon treatment with 2-AP 4 to 5 hours before transduction, 3 to 4 hours before transduction, 2 to 3 hours before transduction, 1 to 2 hours before transduction, 30 minutes to 1 hour before transduction or concurrently to 30 minutes before transduction. In a specific embodiment of the methods described herein, transduction (e.g., retroviral transduction, for example lentiviral transduction) of T lymphocytes (e.g., primary human T lymphocytes) can be enhanced upon treatment with 2-AP both before and concurrently with transduction at any of the time points described herein.

5.1.5. Viral Transduction

In one embodiment of the methods described herein, transduction (e.g., retroviral transduction, for example lentiviral transduction) of T lymphocytes (e.g., primary human T lymphocytes) can occur using viruses at various multiplicities of infection (MOI). In a specific embodiment of the methods described herein, transduction (e.g., retroviral transduction, for example lentiviral transduction) of T lymphocytes (e.g., primary human T lymphocytes) occurs at a viral multiplicity of infection (MOI) of 0.1, 0.2, 0.4, 0.6, 0.8, 1.0, 1.2, 1.4, 1.6, 1.8, 2.0, 2.2, 2.4, 2.6, 2.8, 3.0 or greater. In a specific embodiment of the methods described herein, transduction (e.g., retroviral transduction, for example lentiviral transduction) of T lymphocytes (e.g., primary human T lymphocytes) occurs at a viral multiplicity of infection (MOI) of 0.1 to 0.3, 0.2 to 0.4, 0.4 to 0.6, 0.6 to 0.8, 0.8 to 1.0, 1.0 to 1.2, 1.2 to 1.4, 1.4 to 1.6, 1.6 to 1.8, 1.8 to 2.0, 2.0 to 2.2, 2.2 to 2.4, 2.4 to 2.6, 2.6 to 2.8 or 2.8 to 3.0.

In a specific embodiment of the methods described herein, contacting T lymphocytes (e.g., primary human T lymphocytes) with a compound (e.g., BX795 or 2-AP) to increase transduction efficiency (e.g., lentiviral transduction efficiency) improves the transduction of isolated nucleic acid sequences (e.g., vectors encoding chimeric antigen receptors). For example, nucleic acid sequences of 9 kilobases (kb) in length, 10 kb in length, 11 kb in length, 12 kb in length, 13 kb in length, 14 kb in length, 15 kb in length, 16 kb in length, 17 kb in length or 18 kb in length or greater can be transduced into cells at greater efficiency as a result of the methods described herein (i.e., as compared to the efficiency of transduction in the absence of a compound described (e.g., BX795 or 2-AP)). In certain embodiments, the methods described herein result in improved transduction of nucleic acid molecules (e.g., vectors, for example, viral vectors such as retroviral, e.g., lentiviral, vectors, including vectors that encode one or more proteins, e.g., one or more chimeric antigen receptors), wherein said nucleic acid molecules are 9 kilobases (kb) in length to 10 kb in length, 10 kb in length to 11 kb in length, 11 kb in length to 12 kb in length, 12 kb in length to 13 kb in length, 13 kb in length to 14 kb in length, 14 kb in length to 15 kb in length, 15 kb in length to 16 kb in length, 16 kb in length to 17 kb in length, 17 kb in length to 18 kb in length, or 9 to 18 kb in length or 10 to 15 kb in length.

In a particular aspect of the methods described herein, T lymphocytes (e.g., primary human T lymphocytes) can be transduced (e.g., transduced a retrovirus, for example a lentivirus) with two or more different isolated nucleic acids, e.g., two, three, four or five nucleic acids of non-identical sequence. In a specific embodiment, contacting T lymphocytes (e.g., primary human T lymphocytes) with a compound to increase transduction efficiency (e.g., retroviral transduction efficiency, for example lentiviral transduction efficiency) improves the transduction of one, two, three, four or five different isolated nucleic acids (e.g., vectors, for example, viral vectors, such as retroviral, e.g., lentiviral, vectors, including vectors that encode one or more proteins, for example, encode one or more chimeric antigen receptors).

In a specific embodiment of the methods described herein, primary human T lymphocytes are stimulated for 24 hours with anti-CD3 and/or anti-CD28 antibodies, or antigen binding fragment(s) thereof, in the presence of 50 U/ml IL-2 and 10 μg/ml DEAE-Dextran, followed by treatment of said lymphocytes with BX795 for 3 hours, followed by lentiviral transduction of said lymphocytes, wherein the virus is at a multiplicity of infection (MOI) of 1.8 and wherein the human T lymphocytes are treated with 6 μM BX795 concurrently with the addition of the lentivirus for a further 6 hour period.

In a specific embodiment of the methods described herein, primary human T lymphocytes are stimulated for 24 hours with anti-CD3 and/or anti-CD28 antibodies, or antigen binding fragment(s) thereof, in the presence of 50 U/ml IL-2 and 10 μg/ml DEAE-Dextran, followed by treatment of said lymphocytes with 2-AP for 5 hours, followed by lentiviral transduction of said lymphocytes, wherein the virus is at a multiplicity of infection (MOI) of 1.8 and wherein the human T lymphocytes are treated with 2.5-10 μM 2-AP concurrently with the addition of the lentivirus for a further 5 hour period.

In a specific embodiment of the methods described herein, primary human T lymphocytes are stimulated for 24 hours with anti-CD3 and/or anti-CD28 antibodies, or antigen binding fragment(s) thereof, in the presence of 50 U/ml IL-2 and 10 μg/ml protamine sulfate, followed by treatment of said lymphocytes with BX795 for 6 hours, followed by lentiviral transduction of said lymphocytes, wherein the virus is at a multiplicity of infection (MOI) of 1.8 and wherein the human T lymphocytes are treated with 6 μM BX795 concurrently with the addition of the lentivirus for a further 6 hour period.

In a specific embodiment of the methods described herein, primary human T lymphocytes are stimulated for 24 hours with anti-CD3 and/or anti-CD28 antibodies, or antigen binding fragment(s) thereof, in the presence of 50 U/ml IL-2 and 10 μg/ml protamine sulfate, followed by treatment of said lymphocytes with 2-AP for 5 hours, followed by lentiviral transduction of said lymphocytes, wherein the virus is at a multiplicity of infection (MOI) of 1.8 and wherein the human T lymphocytes are treated with 2.5-10 μM 2-AP concurrently with the addition of the lentivirus for a further 5 hour period.

5.2. Chimeric Antigen Receptors

In certain embodiments, the methods provided herein are used to transduce a nucleic acid encoding one or more chimeric antigen receptor (CARs) into a cell, e.g., a T lymphocyte (e.g., a primary T lymphocyte). CARs are artificial membrane-bound proteins that direct a T lymphocyte to an antigen, and stimulate the T lymphocyte to kill cells displaying the antigen. See, e.g., Eshhar, U.S. Pat. No. 7,741,465. Generally, CARs comprise an extracellular domain that binds to an antigen, e.g., an antigen on a cell, a transmembrane domain, and an intracellular (cytoplasmic) signaling domain that transmits a primary activation signal to an immune cell. All other conditions being satisfied, when a CAR is expressed on the surface of, e.g., a T lymphocyte, and the extracellular domain of the CAR binds to an antigen, the intracellular signaling domain transmits a signal to the T lymphocyte to activate and/or proliferate, and, if the antigen is present on a cell surface, to kill the cell expressing the antigen. Because T lymphocytes require two signals, a primary activation signal and a costimulatory signal, in order to maximally activate, CARs can comprise a stimulatory and a costimulatory domain such that binding of the antigen to the extracellular domain results in transmission of both a primary activation signal and a costimulatory signal.

5.2.1. General CAR Structure Intracellular Domain

In certain embodiments, the intracellular domain of the CAR is or comprises an intracellular domain or motif of a protein that is expressed on the surface of T lymphocytes and triggers activation and/or proliferation of said T lymphocytes. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit.

In certain embodiments, the CAR additionally comprises one or more co-stimulatory domains or motifs, e.g., as part of the intracellular domain of the polypeptide. The one or more co-stimulatory domains or motifs can, for example, be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The transmembrane region can be any transmembrane region that can be incorporated into a functional CAR, e.g., a transmembrane region from a CD4 or a CD8 molecule.

In certain embodiments, the intracellular domain can be further modified to encode a detectable, for example, a fluorescent, protein (e.g., green fluorescent protein) or any variants known thereof.

5.2.2. CAR Extracellular Domain

In certain embodiments, the nucleic acid transduced into cells using the methods described herein comprises a sequence that encodes a polypeptide, wherein the extracellular domain of the polypeptide binds to an antigen of interest. In certain embodiments the extracellular domain comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single-chain Fv domain. The single-chain Fv domain can comprise, for example, a VL linked to VH by a flexible linker, wherein said VL and VH are from an antibody that binds said antigen.

The antigen to which the extracellular domain of the polypeptide binds can be any antigen of interest, e.g., can be an antigen on a tumor cell. The tumor cell may be, e.g., a cell in a solid tumor, or a cell of a blood cancer. The antigen can be any antigen that is expressed on a cell of any tumor or cancer type, e.g., cells of a lymphoma, a lung cancer, a breast cancer, a prostate cancer, an adrenocortical carcinoma, a thyroid carcinoma, a nasopharyngeal carcinoma, a melanoma, e.g., a malignant melanoma, a skin carcinoma, a colorectal carcinoma, a desmoid tumor, a desmoplastic small round cell tumor, an endocrine tumor, an Ewing sarcoma, a peripheral primitive neuroectodermal tumor, a solid germ cell tumor, a hepatoblastoma, a neuroblastoma, a non-rhabdomyosarcoma soft tissue sarcoma, an osteosarcoma, a retinoblastoma, a rhabdomyosarcoma, a Wilms tumor, a glioblastoma, a myxoma, a fibroma, a lipoma, or the like. In more specific embodiments, said lymphoma can be chronic lymphocytic leukemia (small lymphocytic lymphoma), B-cell prolymphocytic leukemia, lymphoplasmacytic lymphoma, Waldenström macroglobulinemia, splenic marginal zone lymphoma, plasma cell myeloma, plasmacytoma, extranodal marginal zone B cell lymphoma, MALT lymphoma, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma, T lymphocyte prolymphocytic leukemia, T lymphocyte large granular lymphocytic leukemia, aggressive NK cell leukemia, adult T lymphocyte leukemia/lymphoma, extranodal NK/T lymphocyte lymphoma, nasal type, enteropathy-type T lymphocyte lymphoma, hepatosplenic T lymphocyte lymphoma, blastic NK cell lymphoma, mycosis fungoides, Sezary syndrome, primary cutaneous anaplastic large cell lymphoma, lymphomatoid papulosis, angioimmunoblastic T lymphocyte lymphoma, peripheral T lymphocyte lymphoma (unspecified), anaplastic large cell lymphoma, Hodgkin lymphoma, or a non-Hodgkin lymphoma. In a specific embodiment, in which the cancer is chronic lymphocytic leukemia (CLL), the B cells of the CLL have a normal karyotype. In other specific embodiments, in which the cancer is chronic lymphocytic leukemia (CLL), the B cells of the CLL carry a 17p deletion, an 11q deletion, a 12q trisomy, a 13q deletion or a p53 deletion.

In certain embodiments, the antigen is a tumor-associated antigen (TAA) or a tumor-specific antigen (TSA). In various specific embodiments, without limitation, the tumor-associated antigen or tumor-specific antigen is B cell maturation antigen (BCMA), B cell Activating Factor (BAFF), Her2, prostate stem cell antigen (PSCA), prostate-specific membrane antigen (PSMA) alpha-fetoprotein (AFP), carcinoembryonic antigen (CEA), EGFRvIII, cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD20, CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, vascular endothelial growth factor receptor (VEGFR), the dimeric form of the pyruvate kinase isoenzyme type M2 (tumor M2-PK), an abnormal ras protein, or an abnormal p53 protein.

In certain embodiments, the TAA or TSA is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain embodiments, the TAA or TSA is a carbohydrate or ganglioside, e.g., fuc-GM1, GM2 (oncofetal antigen-immunogenic-1; OFA-I-1); GD2 (OFA-I-2), GM3, GD3, and the like.

In certain embodiments, the TAA or TSA is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAAO205, Mart2, Mum-1, 2, and 3, neo-PAP, myosin class I, OS-9, pml-RARa fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, TPS, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAPi (six-transmembrane epithelial antigen of the prostate 1), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B. Other tumor-associated and tumor-specific antigens are known to those in the art.

Antibodies, and scFvs, that bind to TSAs and TAAs include antibodies and scFVs that are known in the art, as are nucleotide sequences that encode them.

In certain specific embodiments, the antigen is an antigen not considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments of the polypeptides described herein, the extracellular domain is joined to said transmembrane domain directly or by a linker, spacer or hinge polypeptide sequence, e.g., a sequence from CD28 or a sequence from CTLA4.

5.3. Isolated Nucleic Acids

One of skill in the art will appreciate that the methods described herein are not limited to transduction of any particular type of vector and that the transduced vectors are not limited with respect to the particular type of nucleic acid they comprise. Accordingly, it should be understood that vectors comprising nucleic acids used to transduce cells in accordance with the methods described herein may comprise, for example, any nucleic acid that encodes any protein or polypeptide of interest (e.g., CARs).

In certain embodiments, the nucleic acids may be contained within any polynucleotide vector suitable for the transduction of immune cells, e.g., T lymphocytes. For example, T lymphocytes may be transformed or transduced using synthetic vectors, retroviral vectors (e.g., lentiviral vectors), autonomously replicating plasmids, a virus (e.g., a retrovirus, lentivirus, adenovirus, or herpes virus), or the like, containing polynucleotides encoding polypeptides of interest (e.g., chimeric receptors).

In a specific embodiment, retroviral vectors, for example lentiviral vectors, are used in accordance with the methods described herein. Retroviral vectors, for example lentiviral vectors, suitable for transformation or transduction of T lymphocytes include, but are not limited to, e.g., the lentiviral vectors described in U.S. Pat. Nos. 5,994,136; 6,165,782; 6,428,953; 7,083,981; and 7,250,299, the disclosures of which are hereby incorporated by reference in their entireties.

In another specific embodiment, HIV vectors are used in accordance with the methods described herein. HIV vectors suitable for transduction of T lymphocytes include, but are not limited to, e.g., the vectors described in U.S. Pat. No. 5,665,577, the disclosure of which is hereby incorporated by reference in its entirety.

Nucleic acids useful in the production of polypeptides, e.g., within a T lymphocyte, include DNA, RNA, or nucleic acid analogs. Nucleic acid analogs can be modified at the base moiety, sugar moiety, or phosphate backbone, and can include deoxyuridine substitution for deoxythymidine, 5-methyl-2'-deoxycytidine or 5-bromo-2'-deoxycytidine substitution for deoxycytidine. Modifications of the sugar moiety can include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered, morpholino ring, or peptide nucleic acids, in which the deoxyphosphate backbone is replaced by a pseudopeptide backbone and the four bases are retained. See, for example, Summerton and Weller (1997) Antisense Nucleic Acid Drug Dev. 7:187-195; and Hyrup et al. (1996) Bioorgan. Med. Chain. 4:5-23. In addition, the deoxyphosphate backbone can be replaced with, for example, a phosphorothioate or phosphorodithioate backbone, a phosphoroamidite, or an alkyl phosphotriester backbone.

6. EXAMPLES

6.1. Example 1: Primary T Lymphocyte Transduction with Concurrent Exposure to BX795

6.1.1. Concurrent Treatment of Primary Human T Lymphocytes with DEAE-Dextran Facilitates Lentiviral Transduction Primary human T lymphocytes were cultured in RPMI-1640 media supplemented with 10% (v/v) fetal bovine serum, and activated with anti-CD3/CD28 Dynabeads® at a Dynabead:T lymphocyte ratio of 3:1. After 24 hours of activation, 50 U/ml of IL-2 was added to the culture medium either with or without DEAE-Dextran (DD). Lentivirus encoding the vector JL28.2 (VEGFR2-CD28TM-CD28IC-P2A-GFP), which encodes a chimeric antigen receptor composed of VEGFR2 and GFP protein, was added to the activated T lymphocyte culture at a multiplicity of infection (MOI) of 1.8. Fluorescence-activated cell sorting (FACS) was used to determine the proportion of T lymphocytes expressing VEGFR2 as a marker for successfully transduced cells. As shown in FIG. 1A, 2.61% of mock-treated cells (i.e. cells that received no virus) were VEGFR2$^+$, 3.99% of cells incubated with lentivirus but without DD were VEGFR2$^+$, whereas 9.80% of cells incubated with lentivirus and DD were VEGFR2$^+$. Thus, it was determined that treatment of primary human T lymphocytes with DEAE-dextran facilitates lentiviral transduction.

Figure 1B:
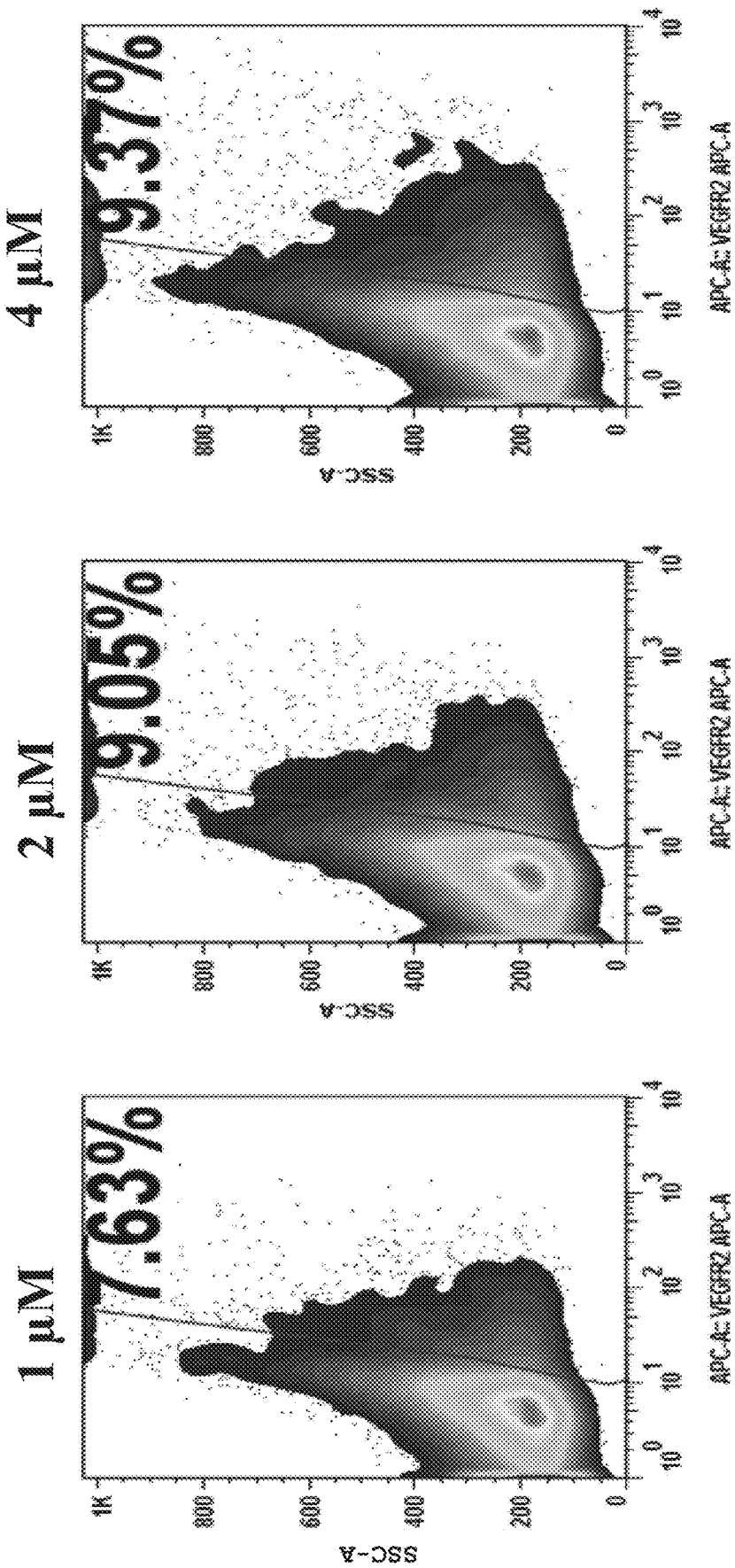
Figure 1C:
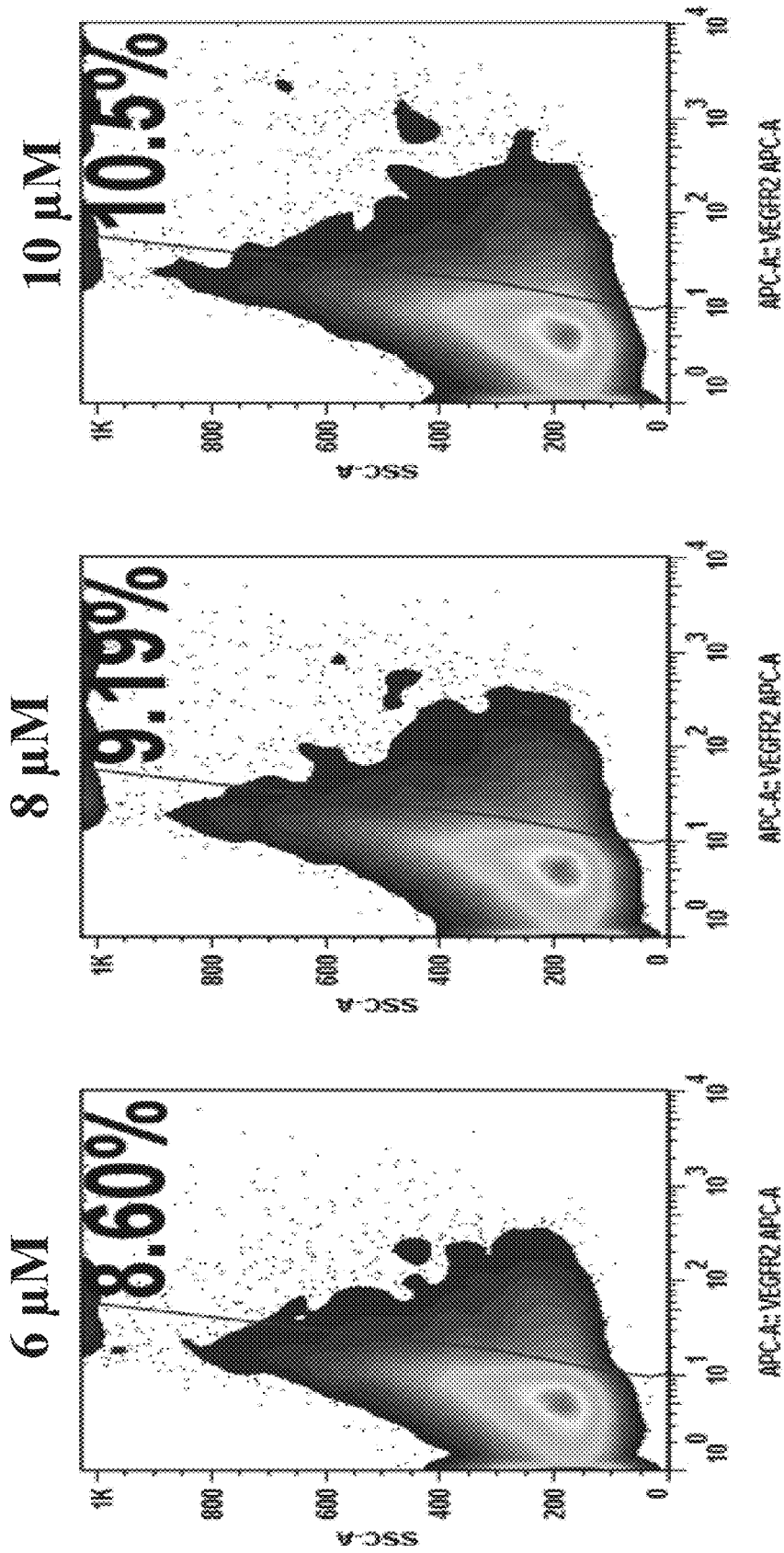

6.1.2. Concurrent Treatment with BX795 Enhances Transduction Efficiency of Primary Human T Lymphocytes Primary human T lymphocytes were cultured and activated as in Section 6.1.1 and transduced with vector JL28.2 in the presence of DEAE-Dextran (DD) and a range of concentrations of BX795, which was added concurrently with the lentivirus and allowed to incubate for six hours. Transduced lymphocytes were then analyzed by FACS to determine the proportion of successfully transduced cells. As shown in FIGS. 1B and 1C, there was an increase in viral transduction efficiency that correlated with increased concentration of BX795 (7.63% of transduced cells were VEGFR2$^+$ when treated with 1 µM BX795 and 10.5% of transduced cells were VEGFR2$^+$ when treated with 10 µM BX795). Thus, it was determined that concurrent treatment of T lymphocytes with lentivirus and BX795 at high dose (10 µM) results in increased transduction efficiency of the cells by lentiviral vectors.

6.2. Example 2: Pretreatment with BX795 is Required for Increased Transduction Efficiency of Primary Human T Lymphocytes Primary human T lymphocytes were cultured and activated as described in Example 1, but with one cell population being treated with DD alone ("DD Only Control"), one cell population being treated with 6 µM BX795 added concurrently with lentiviral transduction for a period of six hours ("Concurrent"), one cell population being treated with 6 µM BX795 for three hours before lentiviral transduction ("Pre-treated") and one cell population being treated with 6 µM BX795 both before and concurrently with lentiviral transduction for a total time period of nine hours ("Pre-treated+Concurrent").

Figure 2B:
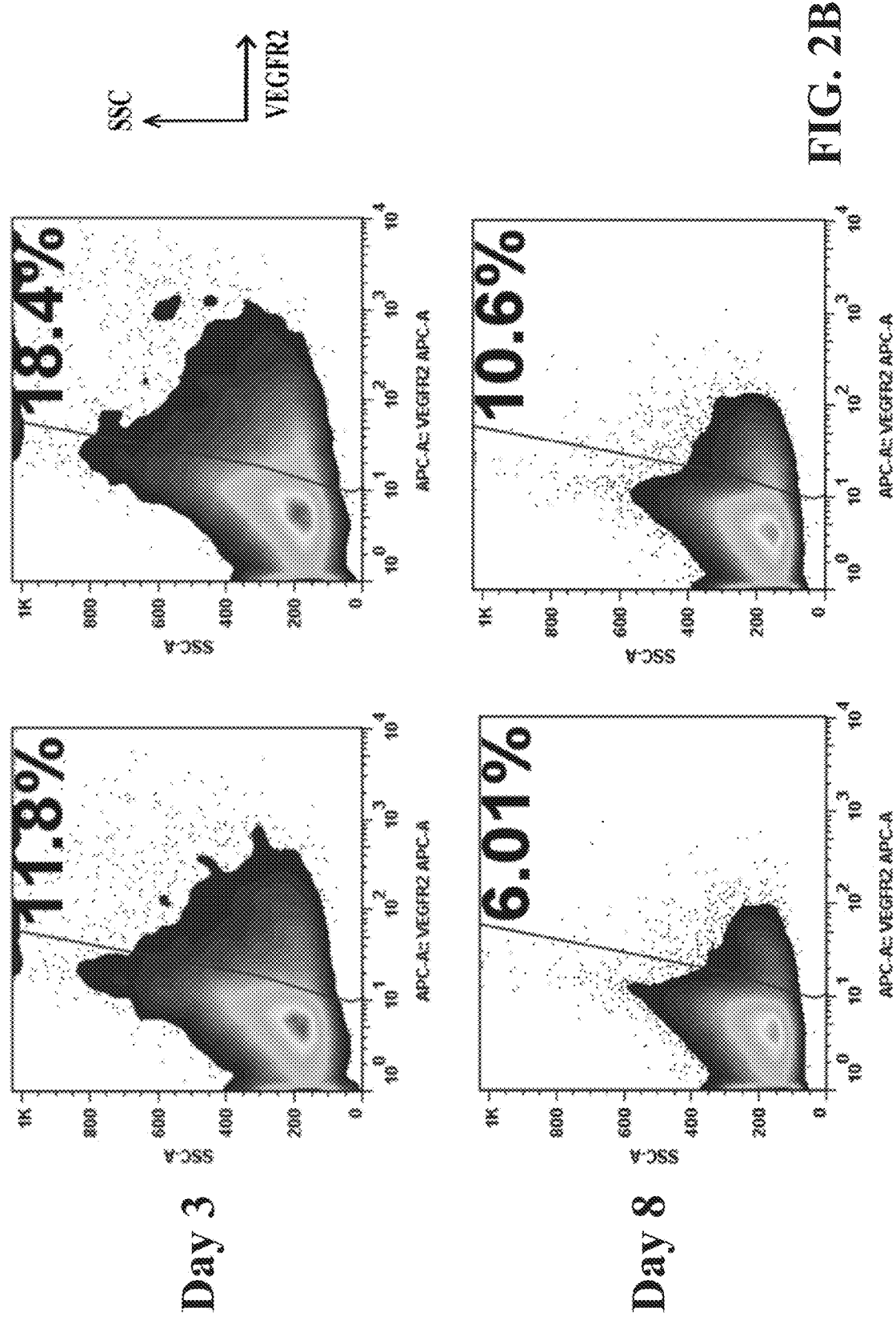

T lymphocytes were cultured for eight days after transduction, and VEGFR2 expression was monitored at days 3 and 8 post-transduction. As shown in FIGS. 2A and 2B, BX795 added to T lymphocyte cultures concurrently with lentivirus showed no improvement in VEGFR2 expression at either day 3 or day 8 as compared to DD Only Control cultures. Pre-treatment of T lymphocytes with BX795 led to an increase in VEGFR2 expression at both day 3 and day 8 as compared to DD Only Control cultures. T lymphocyte cultures treated with BX795 both before and during lentiviral transduction expressed VEGFR2 at a level roughly twice as high as DD Only cultures and higher than either of the other two BX795 treated lymphocytes (9.80% of cells were VEGFR2+ in the DD Only Control at day 3 as compared to 18.4% VEGFR2+ cells in the Pre-treated+Concurrent group at day 3; and 4.95% of cells were VEGFR2+ in the DD Only Control at day 8 as compared to 10.6% VEGFR2+ cells in the Pre-treated+Concurrent group).

6.3. Example 3: Treatment of Primary Human T-Lymphocytes with 2-Aminopurine 6.3.1. 2-Aminopurine does not Alter Cell Viability Primary human T lymphocytes were cultured in RPMI-1640 media supplemented with 10% (v/v) fetal bovine serum (FBS), and activated with anti-CD3/CD28 Dynabeads® at a Dynabead:T lymphocyte ratio of 3:1 for 24 hours. 2-Aminopurine (2-AP) was added to cultures and incubated for 90 minutes at 37 C. DEAE-dextran (DD) or protamine sulfate (PS) were added to the cultures in the presence of 50 U/ml IL-2 and JL28.2 lentiviral vector at an MOI of 3. Cells were analyzed by FACS for viability.

Figure 3A:
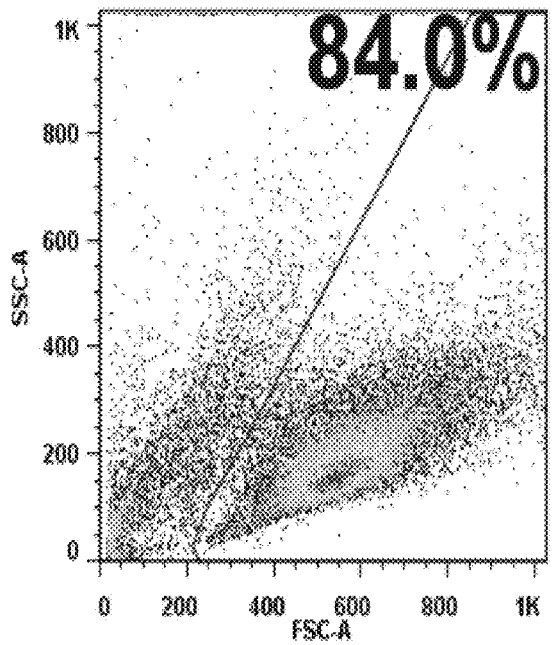
FIGS. 3A and 3B show the effects of the transformation reagents DEAE-dextran and protamine sulfate on the viability of primary human T lymphocytes (FIG. 3A) and the effects of various concentrations of 2-AP in the presence of DEAE-dextran or protamine sulfate on the viability of primary human T lymphocytes transduced with lentivirus (FIG. 3B).
Figure 3A:
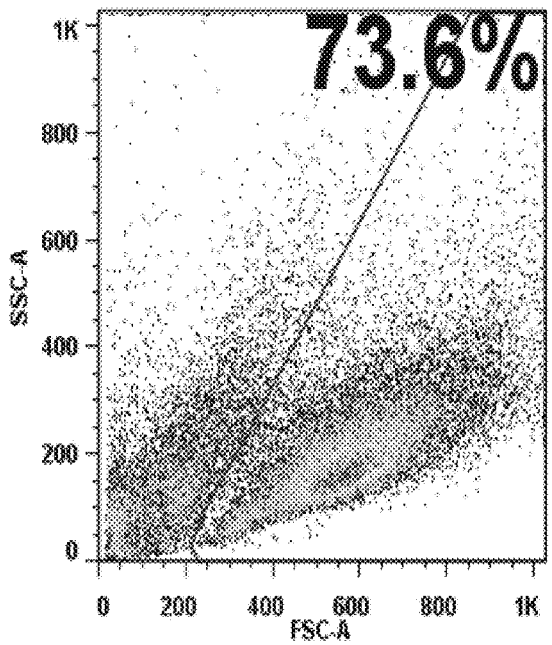
Figure 3A:
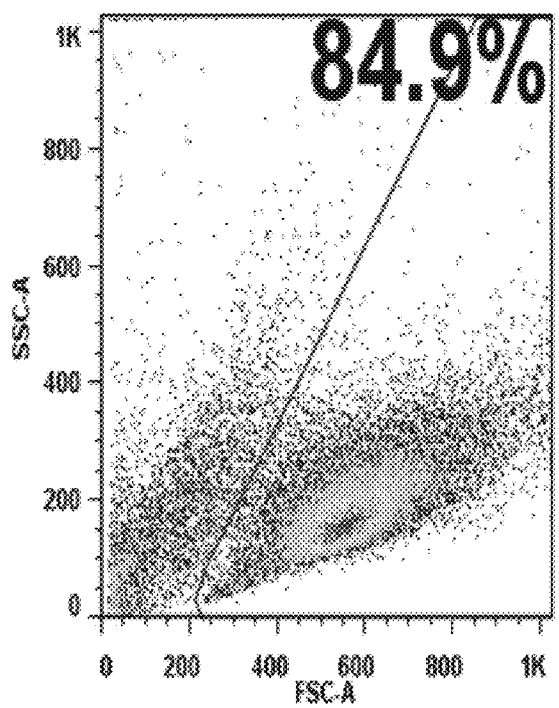
Figure 3A:
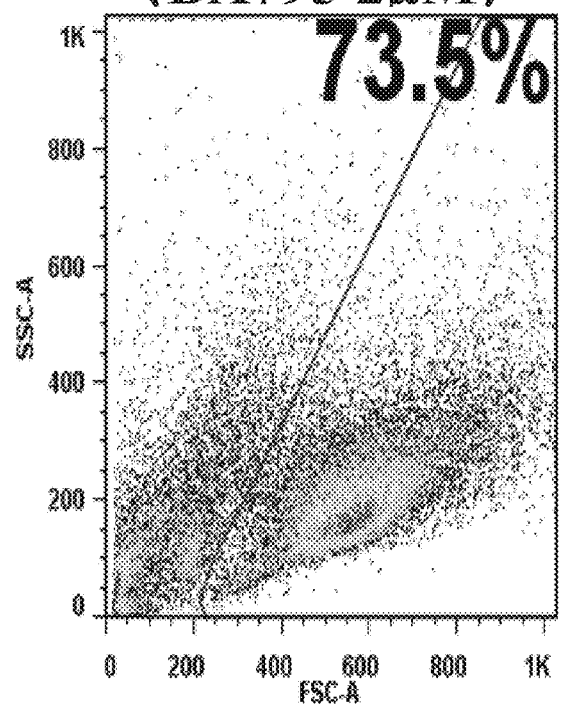
Figure 3B:
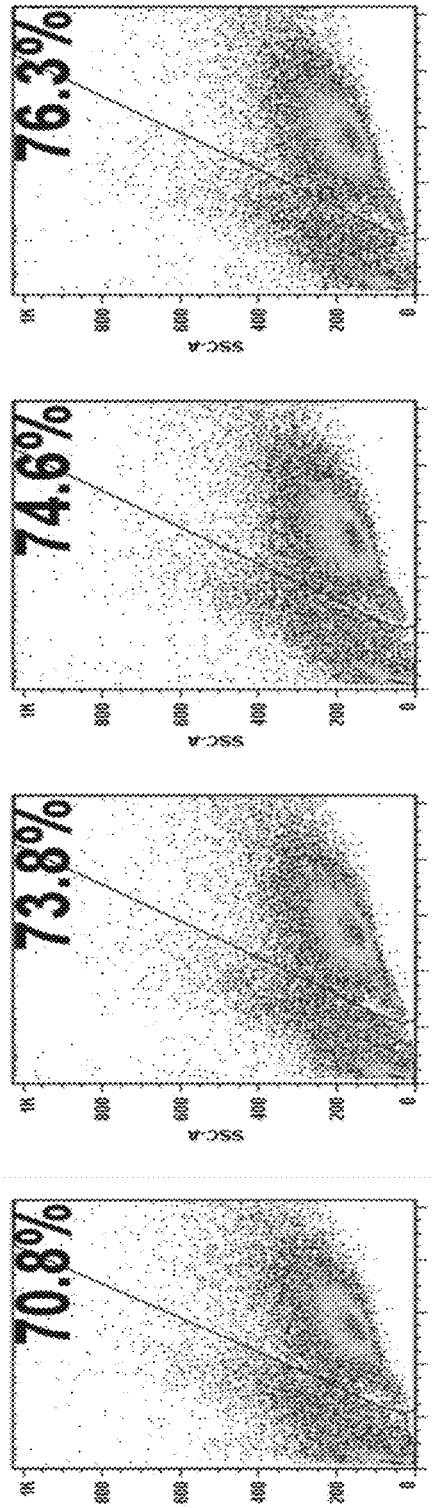
Figure 4A:
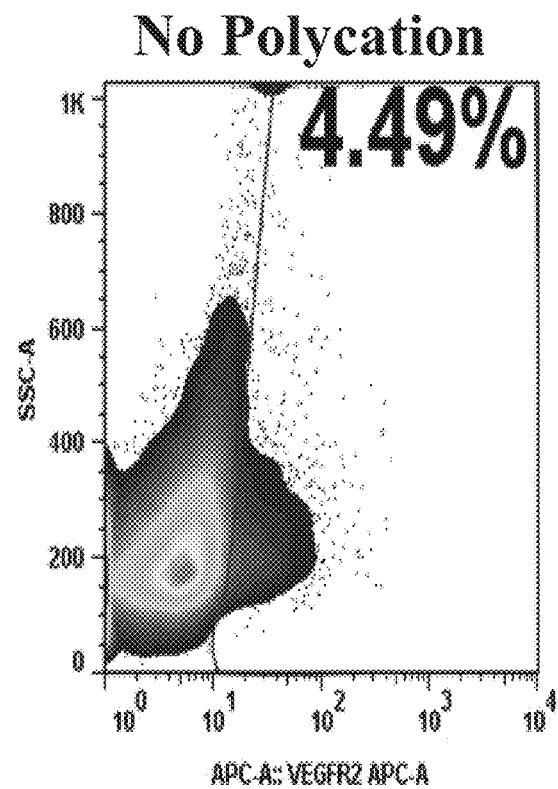
FIGS. 4A and 4B show the efficiency of lentiviral transduction in the absence of 2-AP (FIG. 4A) or in the presence of increasing concentrations of 2-AP (FIG. 4B at concentrations of 2.5 μM, 5 μM or 10 μM).
Figure 4A:
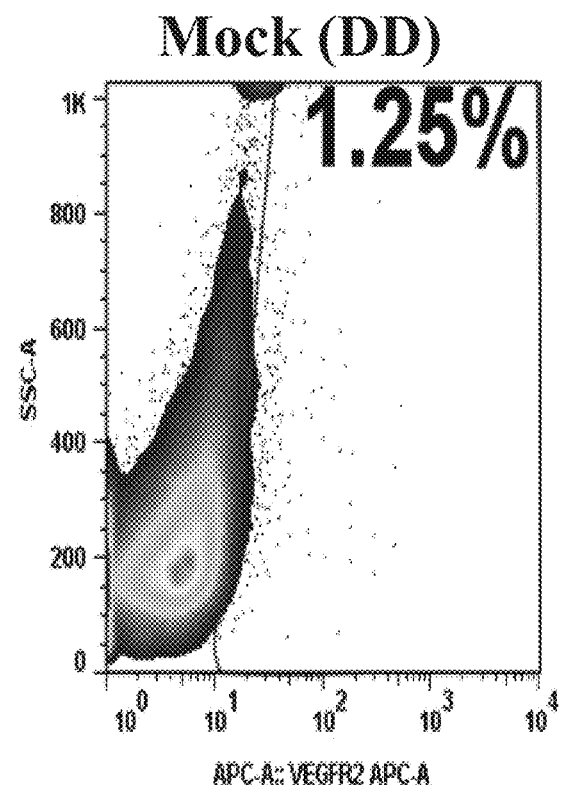
Figure 4A:
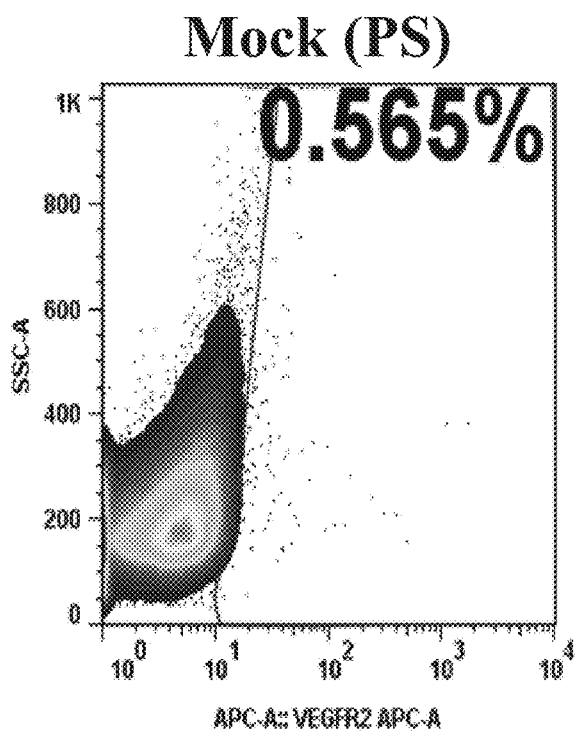
Figure 4A:
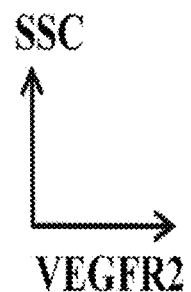

In the absence of 2-AP, 84% of cells treated without either DD or PS were viable after lentiviral transduction, while 73.6% of cells were viable when transduced in the presence of DD, and 84.9% of cells were viable when transduced in the presence of PS. (FIG. 3A) When primary T lymphocytes were cultured as above with the addition of 2-AP at either 2.5 mM, 5 mM or 10 mM, viability was not reduced compared to cells cultured in the absence of 2-AP (FIG. 3B), indicating that 2-AP does not alter the viability of activated primary human T-lymphocytes in culture. 6.3.2. Treatment with 2-Aminopurine enhances lentiviral transduction efficiency of primary human T lymphocytes Primary human T lymphocytes were cultured as in Section 6.3.1 and analyzed by FACS for expression of VEGFR2. As shown in FIG. 4A, 4.49% of cells transduced with lentivirus in the absence of either DD or PS were positive for VEGFR2, while 1.25% of cells treated with DD alone were VEGFR2+ and 0.565% of cells treated with PS alone were VEGFR2+.

Figure 4B:
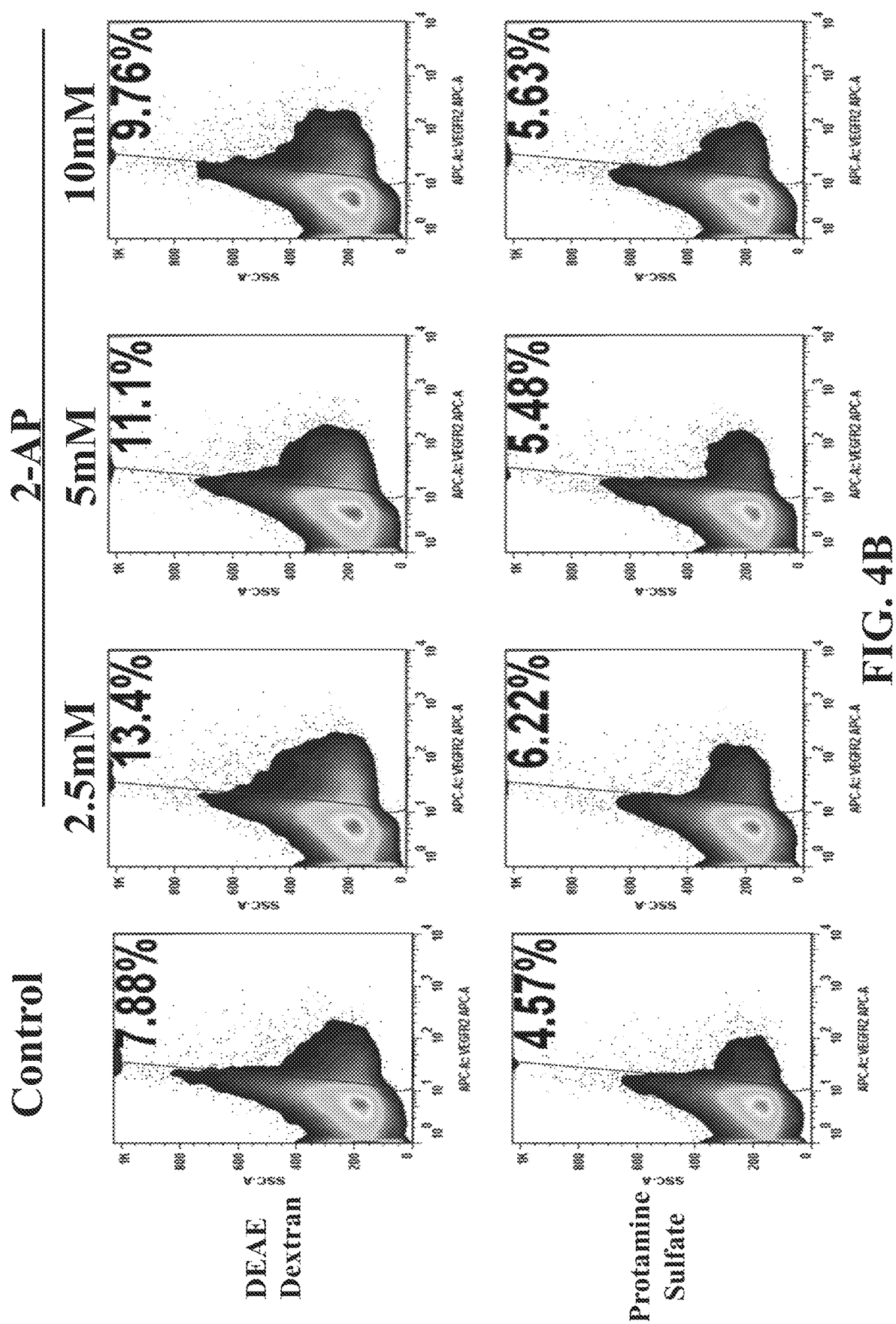

In the presence of either DD or PS, lentiviral transduction was enhanced when primary T lymphocytes were pretreated with 2-AP for 90 minutes and maintained in culture with lentivirus and various concentrations of 2-AP for 5 hours (FIG. 4B). All concentrations of 2-AP (i.e., 2.5 mM, 5 mM or 10 mM) increased transduction efficiency as compared to cells not exposed to 2-AP (Control). These results indicate that treatment with 2-AP increases the transduction efficiency of primary human T lymphocytes in the presence of either DEAE-dextran or protamine sulfate.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A method of transducing a primary T lymphocyte, comprising:
   (i) contacting a primary T lymphocyte with a compound that is an inhibitor of the innate immune system and inhibits the activity of protein kinase R (PKR); and
   (ii) contacting the primary T lymphocyte with a viral vector comprising a nucleic acid;
   wherein the contacting of the primary T lymphocyte with the compound occurs prior to the contacting of the primary T lymphocyte with the viral vector;
   whereby the nucleic acid is transduced into the primary T lymphocyte.

2. The method of claim 1, wherein the primary T lymphocyte is a human primary T lymphocyte.

3. The method of claim 1, wherein the contacting of the primary T lymphocyte with the compound occurs concurrently with the contacting with the viral vector.

4. The method of claim 1, wherein the nucleic acid is about 9 to 20 kb in length.

5. The method of claim 1, wherein the nucleic acid encodes a chimeric antigen receptor.

6. The method of claim 1, wherein the compound is is 2.5-10 µM 2-aminopurine.

7. The method of claim 6, wherein the 2-aminopurine is 2.5-10 µM 2-aminopurine.

8. The method of claim 1, further comprising contacting the primary T lymphocyte with an agent capable of stimulating a T cell receptor complex prior to the contacting of the primary T lymphocyte with the viral vector.

9. The method of claim 8, wherein the agent is an antibody or antigen-binding fragment that specifically binds to CD3 or CD28.

10. The method of claim 1, wherein the viral vector is a retroviral vector.

11. The method of claim 1, wherein the viral vector contacts the primary T lymphocyte at a multiplicity of infection (MOI) of 1.5 to 2.5.

12. The method of claim 1, further comprising contacting the primary T lymphocyte with a transformation reagent and a cytokine.

13. The method of claim 12, wherein the transformation reagent is diethylaminoethyl-dextran.

14. The method of claim 12, wherein the cytokine is interleukin 2 (IL-2).

15. A method of transducing a human primary T lymphocyte, comprising:
   (i) contacting a human primary T lymphocyte, in the presence of diethylaminoethyl-dextran and interleukin 2 (IL-2), with 2-aminopurine; and
   (ii) contacting the human primary T lymphocyte with a lentiviral vector comprising a nucleic acid encoding a chimeric antigen receptor;
   wherein the contacting of the human primary T lymphocyte with the 2-aminopurine occurs prior to the contacting of the human primary T lymphocyte with the lentiviral vector;
   whereby the nucleic acid is transduced into the T lymphocyte.

16. The method of claim 1, wherein the contacting of the primary T lymphocyte with the compound occurs for 90 minutes prior to the contacting of the primary T lymphocyte with the viral vector.

17. The method of claim 1, wherein the contacting of the primary T lymphocyte with the viral vector and the compound occurs concurrently for at least 5 hours.

18. The method of claim 1, wherein the contacting of the primary T lymphocyte with the compound occurs after the contacting with the viral vector.

19. The method of claim 1, wherein the viral vector is a lentiviral vector.

20. The method of claim 12, wherein the transformation reagent is protamine sulfate.

21. The method of claim 1, wherein the contacting of the primary T lymphocyte with the compound occurs for 5 hours, 4 hours, 3 hours, 2 hours, 1 hour, 30 minutes, 15 minutes, or 5 minutes prior to the contacting of the primary T lymphocyte with the viral vector.

22. The method of claim 1, wherein the contacting of the primary T lymphocyte with the viral vector and the compound occurs concurrently for 5 hours, 4 hours, 3 hours, 2 hours, 1 hour, 30 minutes, 15 minutes, or 5 minutes.

* * * * *